United States Patent
Lemke et al.

(10) Patent No.: US 11,988,797 B2
(45) Date of Patent: May 21, 2024

(54) MOISTURE DETECTION SYSTEMS AND DEVICES

(71) Applicants: John Lemke, Hudson, FL (US); Martha Lemke, Hudson, FL (US)

(72) Inventors: John Lemke, Hudson, FL (US); Martha Lemke, Hudson, FL (US); Paul Latten, Clover, SC (US)

(73) Assignees: John Lemke, Hudson, FL (US); Martha Lemk, Hudson, FL (US)

( * ) Notice: Subject to any disclaimer, the term of this patent is extended or adjusted under 35 U.S.C. 154(b) by 0 days.

(21) Appl. No.: 18/316,607

(22) Filed: May 12, 2023

(65) Prior Publication Data

US 2023/0367028 A1 Nov. 16, 2023

Related U.S. Application Data

(60) Provisional application No. 63/370,713, filed on Aug. 8, 2022, provisional application No. 63/356,253, filed on Jun. 28, 2022, provisional application No. 63/342,195, filed on May 16, 2022.

(51) Int. Cl.
*G01V 3/04* (2006.01)
*A61F 13/42* (2006.01)

(52) U.S. Cl.
CPC ............ *G01V 3/04* (2013.01); *A61F 13/42* (2013.01); *A61F 2013/424* (2013.01)

(58) Field of Classification Search
CPC ...... G01V 3/04; A61F 13/42; A61F 2013/424
See application file for complete search history.

(56) References Cited

U.S. PATENT DOCUMENTS

| | | | |
|---|---|---|---|
| 2,687,721 | A | 8/1954 | Ellison |
| 3,460,123 | A | 8/1969 | Bass |
| 4,919,950 | A | 4/1990 | Mak |
| 8,299,317 | B2 | 10/2012 | Tippey et al. |
| 8,381,575 | B2 | 2/2013 | Seo |
| 8,697,934 | B2 | 4/2014 | Nhan et al. |
| 8,914,923 | B2 | 12/2014 | Smith |
| 10,350,115 | B2 | 7/2019 | Long et al. |
| 10,987,052 | B2 | 4/2021 | Macia Barber et al. |

(Continued)

*Primary Examiner* — Christopher P McAndrew
*Assistant Examiner* — Zannatul Ferdous
(74) *Attorney, Agent, or Firm* — Shumaker, Loop & Kendrick, LLP; Jeffrey B. Fabian (57) ABSTRACT

Disclosed herein are systems and devices which are capable of detecting moisture and remotely indicating when the presence of moisture is detected. The systems utilize multilayer sensors that consist of two conductive layers surrounding an insulating, spacer layer. Nonwoven materials with conductive additives have shown particular advantages for use in constructing the conductive sensor layers. The multilayer sensor can be electrically coupled to a transmitter that is itself in electrical communication with one or more receiver devices. The transmitter and receiver devices are configured to provide indicators when moisture is detected through audible signals, vibration, visible signals or through notifications displayed on a software application. The sensor and/or the transmitter may be attached along a perimeter of the layers. The layered sensor may be affixed to an inside or outside of a package for location tracking, or may be attached to or incorporated in a diaper, as non-limiting examples.

21 Claims, 10 Drawing Sheets

(56) References Cited

U.S. PATENT DOCUMENTS

| | | | | |
|---|---|---|---|---|
| 2009/0036015 A1* | 2/2009 | Nhan | ................... | D21H 13/36 |
| | | | | 442/335 |
| 2009/0036850 A1* | 2/2009 | Nhan | ................... | A61F 13/42 |
| | | | | 604/385.01 |
| 2012/0055641 A1* | 3/2012 | Nhan | ................ | D04H 1/4234 |
| | | | | 162/138 |
| 2014/0371702 A1* | 12/2014 | Bosaeus | ............ | A61F 13/51484 |
| | | | | 604/385.01 |
| 2016/0374867 A1* | 12/2016 | Zand | ..................... | A61F 13/42 |
| | | | | 604/361 |

\* cited by examiner

MOISTURE DETECTION SYSTEMS AND DEVICES

CROSS-REFERENCE TO RELATED APPLICATION

This application claims the benefit of priority of each of: U.S. provisional patent application No. 63/342,195, titled "Moisture Detection Devices" filed on May 16, 2022; U.S. provisional patent application No. 63/356,253, titled "Moisture Detection Devices," filed on Jun. 28, 2022; U.S. provisional patent application No. 63/370,713, titled "Moisture Detection Devices" filed on Aug. 8, 2022, the contents of all of which are incorporated herein in its entirety by this reference.

TECHNICAL FIELD

The present invention relates to devices which detect moisture and that are capable of remote notification.

BACKGROUND

Existing moisture detection devices rely on conductive electrodes and other electronic components that are disposed or built onto or into absorbent materials that serve to detect unwanted spread of fluids. The detection devices are only triggered when moisture reaches the conductive electrodes. By that time, the absorbent material may have already reached saturation, and the undesired spread of fluid is imminent. Additionally, the electrodes and electronic components come at a significant cost and are prone to corrosion over time. Consequently, the moisture detection devices must be properly disposed of and replaced at regular intervals, which exacerbates cost concerns. Another major concern is when the electrodes accidentally touch each other, like in wrinkling or folding, and causes a false alarm.

Considering the drawbacks of existing devices, it is advantageous to provide moisture detection devices that are capable of detecting moisture at any sensor location and wrinkling or folding will not cause a false alarm. The sensor locations are multiple entire layers, not strips, weaves or threads used on one layer in existing moisture detection devices. The entire sensor layer materials are conductive and coupled to electronic components in a manner that does not expose the electronic components to corrosion and wrinkling or folding will not cause a false alarm.

SUMMARY

This summary is provided to briefly introduce concepts that are further described in the following detailed descriptions. This summary is not intended to identify key features or essential features of the claimed subject matter, nor is it to be construed as limiting the scope of the claimed subject matter.

According to at least one embodiment, a moisture detection system includes a transmitter and a layered sensor connected to the transmitter. The layered sensor includes two conductive layers and a separator layer between the two conductive layers. The conductive layers form a closed circuit in a dry state. The conductive layers form an open or shorted circuit when moisture is present on both of the conductive layers. The transmitter detects an absence of a signal from the formerly closed circuit and interprets the absence of the signal as a positive indicator of moisture.

The above and below described layers may be, but are not limited to, non-woven fabrics.

In some examples, which are non-limiting and do not apply to all implementations, at least one of the two conductive layers includes at least one of conductive strips, conductive weaves, conductive threads, and carbon fibers.

One or both of the two conductive layers may include wetlaid material.

The wetlaid material may be formed by combining conductive fibers with pulp fibers to form nonwoven webs, in a non-limiting example.

In some examples, at least one of the two conductive layers includes and absorbency aid including at least one of a cationic surfactant, an anionic surfactant, a non-ionic surfactant, a humectant, a plasticizer, low molecular weight polyethylene glycol, a polyhydroxy compound, glycerin, and propylene glycol.

The system may include an output device connected to the layered sensor, the closed or complete circuit resulting in an electrical signal causing the output device to output an alert.

The output device may include at least one of a vibrator, a buzzer, and a computing device that displays a notification on an electronic display.

The layered sensor may be disposed on an article of clothing.

The layered sensor may include a moisture wicking layer.

The layered sensor may be affixed to an inside or outside of a package for location tracking.

According to at least one other embodiment, to which the above examples and options apply as well, a moisture detection system includes a transmitter and a layered sensor connected to the transmitter. The layered sensor includes two conductive layers and a separator layer between the two conductive layers. The two conductive layers form an open circuit in a dry state. The conductive layers form a closed or complete circuit when moisture is present between the conductive layers. The closed or complete circuit results in an electrical signal that is detected by the transmitter and interpreted as a positive indicator of moisture.

Various nonwoven technologies and compositions can be used to produce a conductive layer. Three layers may be advantageous for eliminating false alarms caused by folding or wrinkling. The described and/or referenced electronics, their use and combination with the described layered structures, all of which are provided as non-limiting examples, are novel and advantageous. Electronic attachment to the layer may be at any location on the layers, for example anywhere along the perimeter of the layers. These technologies incorporated into or attached to diapers, and other use examples are within the scope of these descriptions.

The above summary is to be understood as cumulative and inclusive. The above described embodiments and features are combined in various combinations in whole or in part in one or more other embodiments.

BRIEF DESCRIPTION OF THE DRAWINGS

The previous summary and the following detailed descriptions are to be read in view of the drawings, which illustrate some, but not all, embodiments and features as briefly described below. The summary and detailed descriptions, however, are not limited to only those embodiments and features explicitly illustrated.

DETAILED DESCRIPTION

The present invention will now be described more fully with reference to the accompanying figures in which example embodiments of the invention are shown. However, the invention may be embodied in many different forms and should not be constrained as limited to the representative embodiments set forth herein. The example embodiments are provided so that this disclosure will be both thorough and complete and fully convey the scope of the invention to enable one of ordinary skill in the art to make, use and practice the invention. The form factor of any component may change from the shape shown in the figures, such as replacing a pyramid shape or cylinder with a box shape.

Relative terms such as lower or bottom; upper or top; upward, outward, or downward; forward or backward; and vertical or horizontal may be used herein to describe one element's relationship to another element illustrated in the figures. It will be understood that relative terms are intended to encompass different orientations in addition to the orientation depicted in the drawings. By way of example, if a component in the drawings is turned over, elements described as being on the "bottom" of the other elements would then be oriented on "top" of the other elements. Relative terminology, such as "substantially" or "about," describe the specified materials, steps, parameters, or ranges as well as those that do not materially affect the basic and novel characteristics of the claimed inventions as whole.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

Disclosed herein are systems and devices capable of absorbing and/or detecting moisture and remotely indicating when the presence of moisture is detected. The systems utilize multilayer sensors where the number and type of layers vary according to the particular application for which the moisture detector is used. The system may utilize multilayer sensors that consist of two conductive layers surrounding an insulating, spacer layer.

Nonwoven materials with conductive additives have shown particular advantages for use in constructing the sensors given the favorable conductive properties, durability, and the ability to tailor the properties of nonwoven materials. The multilayer sensor can be electrically coupled to a transmitter that is itself in electrical communication with one or more receiver devices. The transmitters and receiver devices are configured to provide indicators when moisture is detected through audible signals, vibratory, visible signals, or through notifications displayed by a software application on a computing device.

Products and processed are described herein and are illustrated in the accompanying drawings innovatively using fiber technology, optionally non-woven fiber technology, to detect moisture. Sensors are used to provide wireless alerts. An innovative marriage between material science (such as nonwoven material technology) and electrical engineering is described herein. These description detail novel product concepts to place a nonwoven patch on a wearable garment (a shirt, blouse, and/or vest as non-limiting examples) to detect excessive perspiration (hyperhidrosis) and provide wireless alerts.

Layers—Prior related products and articles typically had a conductive single layer. Various nonwoven technologies can be used to produce a conductive layer. Likewise, various compositions of the layer can be used to produce a conductive layer. All references herein to nonwoven technology and specific compositions are provided as non-limiting examples only.

Three Layers—The combined use of three layers as described herein is advantageous. This results in most likely eliminating false alarms caused by folding or wrinkling. Various nonwoven technologies and compositions can be used to produce these layers. The specific use helps to determine whether and which additional layers are used.

Electronics—The electronics which are identified are provided as non-limiting examples. Their use and combination with the described layered structures are novel and advantageous. Electronic attachment to the layer may be at any location on the layers, for example anywhere along the perimeter of the layers.

Use Examples—The described and illustrated examples provide unique combinations of nonwoven technology and electronics. Prior work by others has focused almost exclusively on diapers. Other use examples described herein are drawn to new, untapped markets. Each use example herein may use a different unwoven technology, layer composition and electronics.

The use of the multilayered sensor approach has the advantage that moisture can change the properties of the insulating or dielectric layer to trigger detection at any point along the cross sectional area to close a circuit, open a circuit, or change the resistance or capacitance. The systems and devices are not dependent upon moisture reaching only certain portions of the sensor that correspond to locations of an electrode since the entirety of the sheets form a detection surface.

Circuit Operations—The multilayer sensors include at least a central insulating sheet layer surrounded on either side by electrically conductive sheet layers. The sensors can be configured for at least two modes of operation—a "short-circuit" mode and a "complete-circuit" mode.

In the short-circuit mode, the sensor includes two conductive layers and a separator layer between the two conductive layers. The conductive layers form a closed circuit in a dry state. The circuit becomes open, or shorted, when moisture is present on both of the conductive layers. The transmitter detects the absence of a signal from the formerly closed circuit and interprets the absence of the signal as a positive indicator of moisture.

For the complete-circuit mode, the conductive layers form an open circuit in a dry state that becomes closed, or complete, when a moisture is present between the layers. The closed circuit results in an electrical signal that is detected by the transmitter and interpreted as a positive indicator of moisture. In other embodiments, the complete-circuit mode utilizes conductive strips, weaves, or threads on one layer to form an open circuit in a dry state. The circuit becomes closed, or complete, when moisture is present and connects two or more strips, weaves or threads. The transmitter detects the presence of a signal from the formerly open, now closed, circuit and interprets the presence of the signal as a positive indicator of moisture.

Figure 1A:
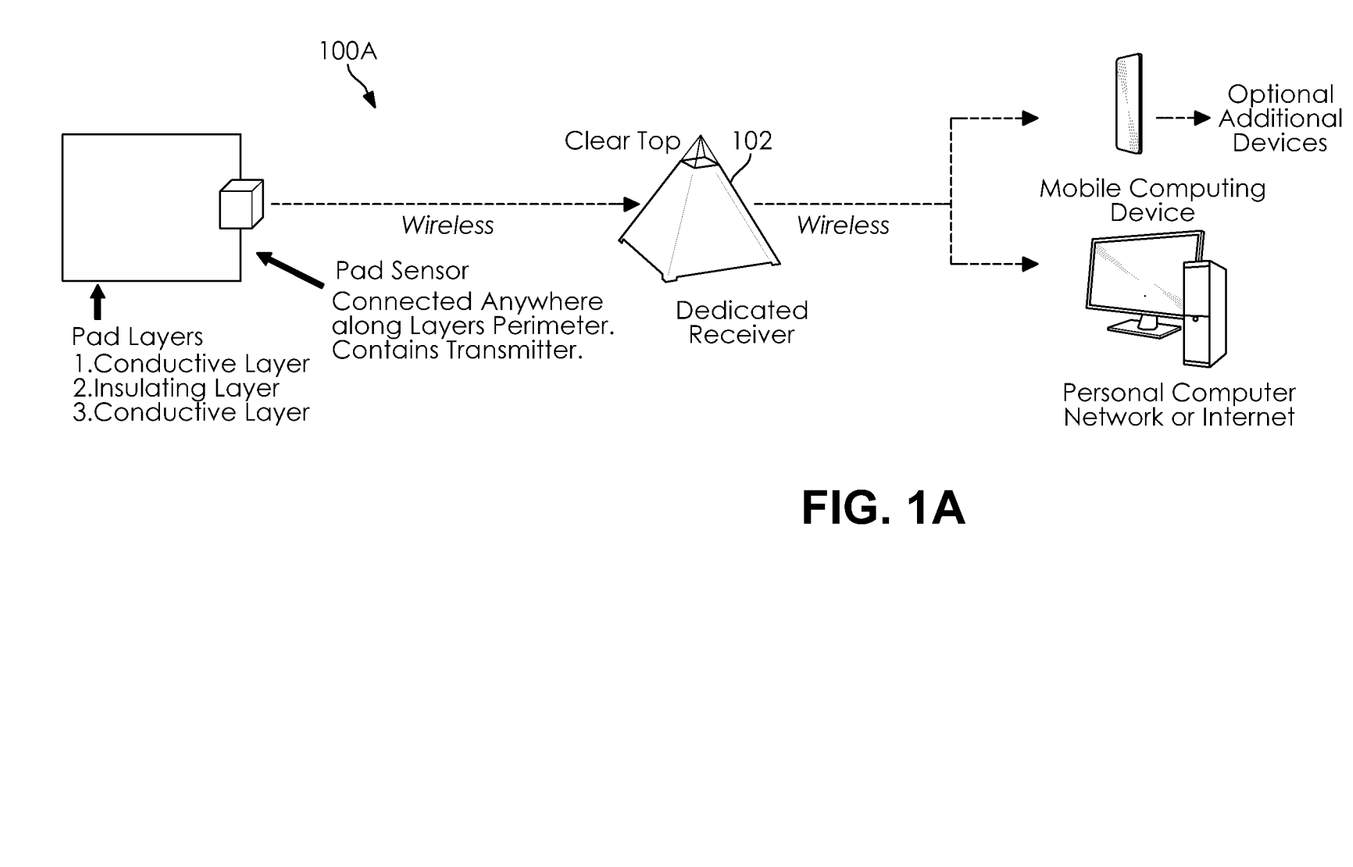
FIG. 1A is an example embodiment of a moisture detection system with a minimum number of pad layers and use of a dedicated receiver.

FIG. 1A illustrates a moisture detection system 100A according to at least one embodiment and configuration. It includes: (i) multilayer sensor; (ii) pad sensor and transmitter which is electrically coupled to the sensor; and (iii) one or more receiver devices in signal communication with the transmitter device.

Figure 1B:
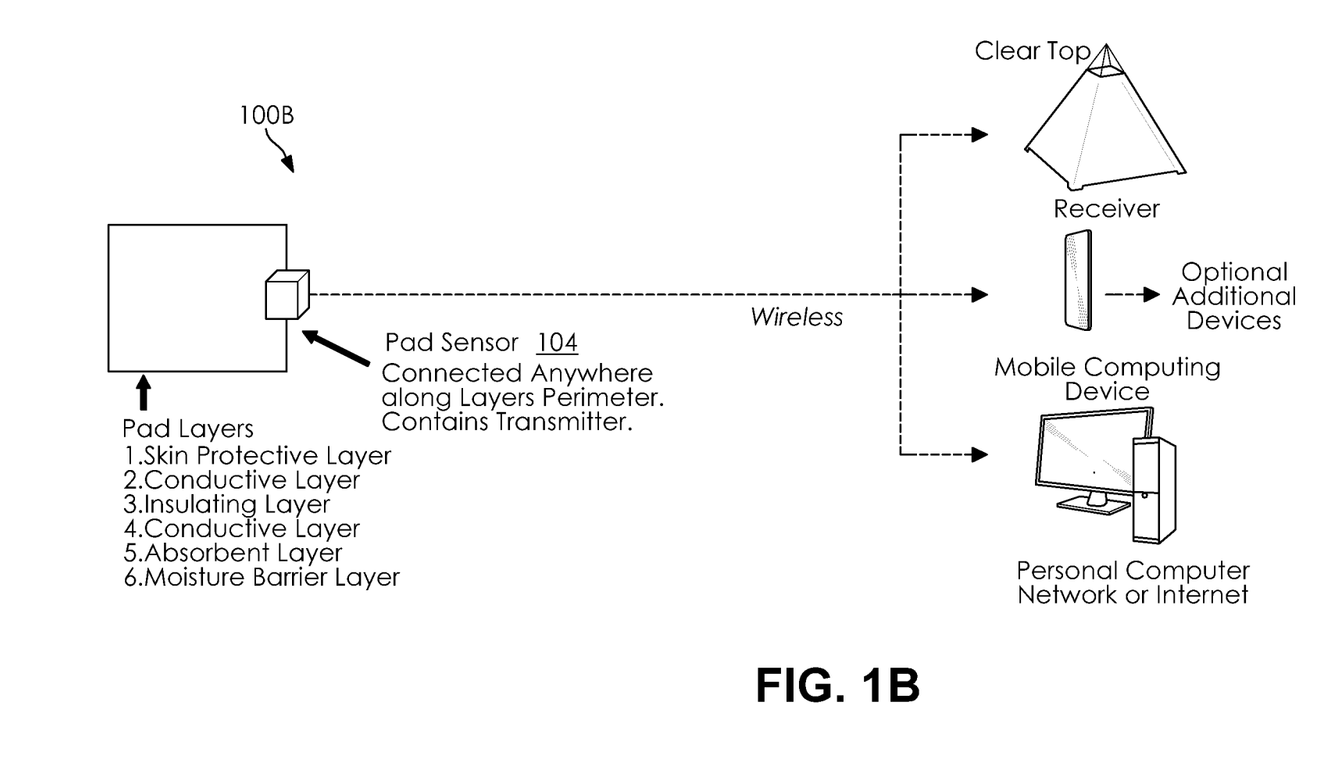
FIG. 1B is an example embodiment of a moisture detection system with additional pad layers and direct connection to mobile and network computers.

FIG. 1B illustrates a moisture detection system 100B according to at least one embodiment and configuration. It includes: (i) multilayer sensor and additional layers for a specific application; (ii) pad sensor and transmitter which is electrically coupled to the sensor; and (iii) one or more receiver devices in signal communication with the transmitter device. Those of ordinary skill in the art will appreciate that the configurations shown in FIGS. 1A and 1B are not intended to be limiting, and other system configurations are possible.

Figure 2A:
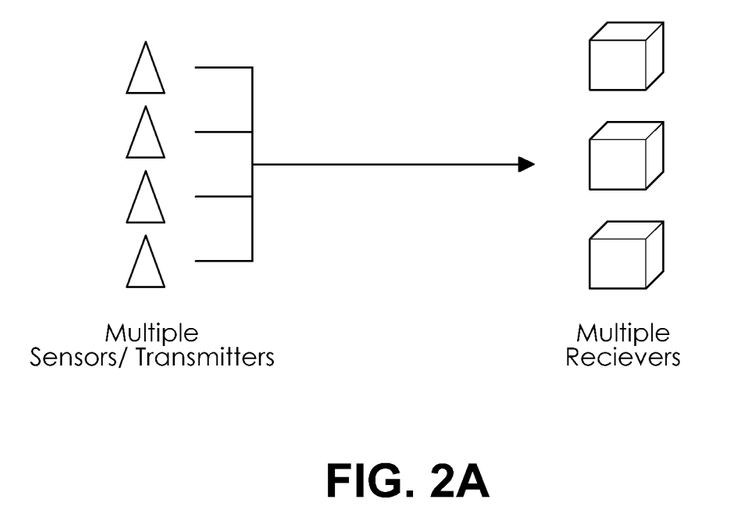
FIG. 2A is an example embodiment of a moisture detection system with multiple sensors/transmitters to multiple receivers.
Figure 2B:
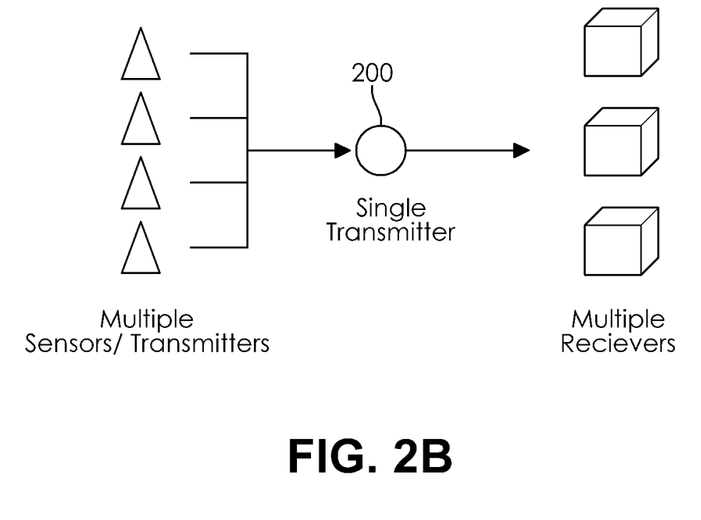
FIG. 2B is an example embodiment of a moisture detection system with multiple sensors and one transmitter to multiple receivers.

FIG. 2A illustrates a configuration where multiple sensor-transmitter devices are in signal communication with multiple receiver devices. FIG. 2B illustrates multiple sensors feeding a single transmitter device that is in signal communication with one or more receiver devices.

Figure 3A:
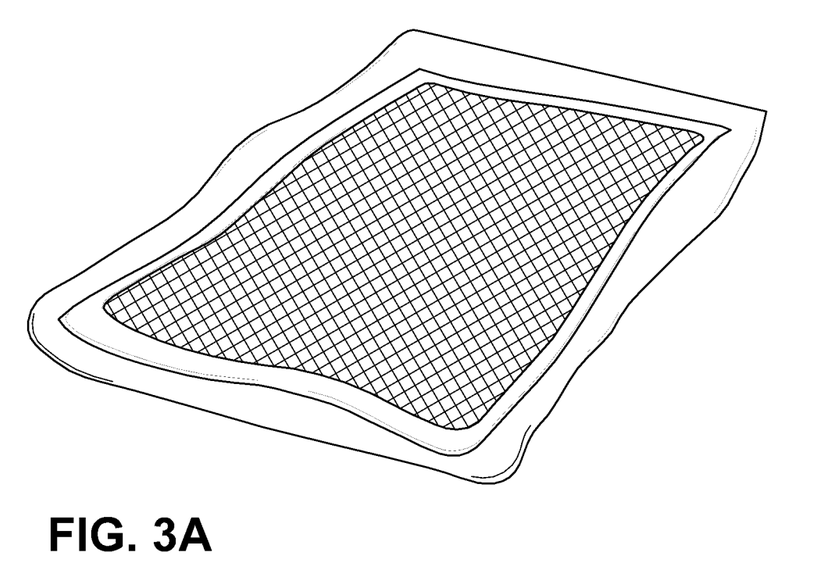
FIG. 3A is an example embodiment of an underpad moisture detection system without an absorbent layer.
Figure 3B:
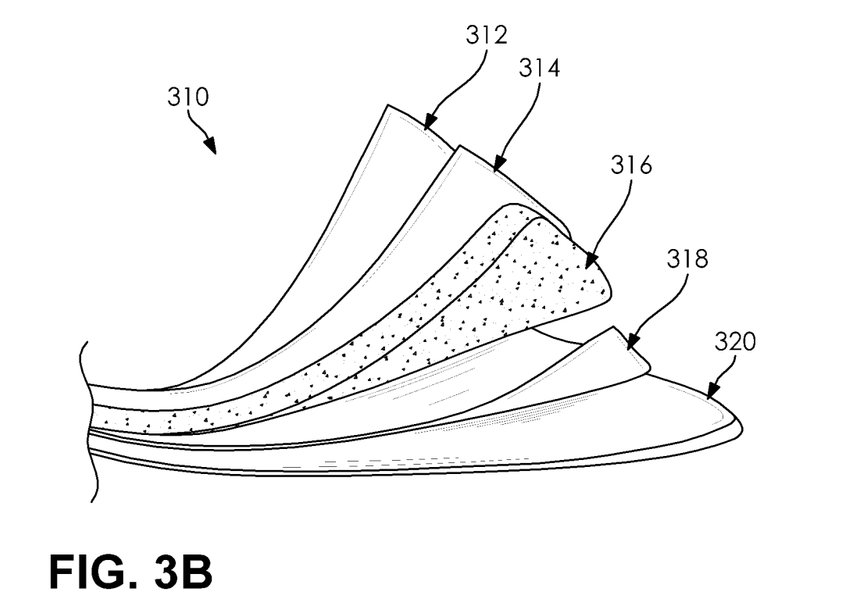
FIG. 3B is an example embodiment of an underpad moisture detection system with an absorbent layer.

FIGS. 3A-3B illustrates a multitude of layers that may apply to specific applications. The number of layers, order of the layers, materials used, and function of the layers varies according to the particular sensor application. For instance, sensors used for personal hygiene products may also include a skin protectant layer and/or a wicking layer to ensure safety and comfort for a user in addition to the sensor layers.

The details of the multilayer sensor are discussed below. In the particularly illustrated embodiment of an underpad sensor 310 of FIG. 3B, having pad layers without an absorbent layer, a skin protective layer 312, a conductive layer 314, an insulating layer 316, a conductive layer 318, and a moisture barrier 320 are shown as a layered assembly. In at least one embodiment, an underpad sensor, with an absorbent layer, includes a skin protective layer, a sensor fabric layer, a separator fabric layer, a sensor fabric layer, an absorbent layer, and a moisture barrier/waterproof layer. The sensor fabric layer, separator fabric layer, and sensor fabric layer are custom designed layers in some examples. The skin protective layer, absorbent layer, and moisture barrier/waterproof layer may be commercially available layers.

Figure 4A:
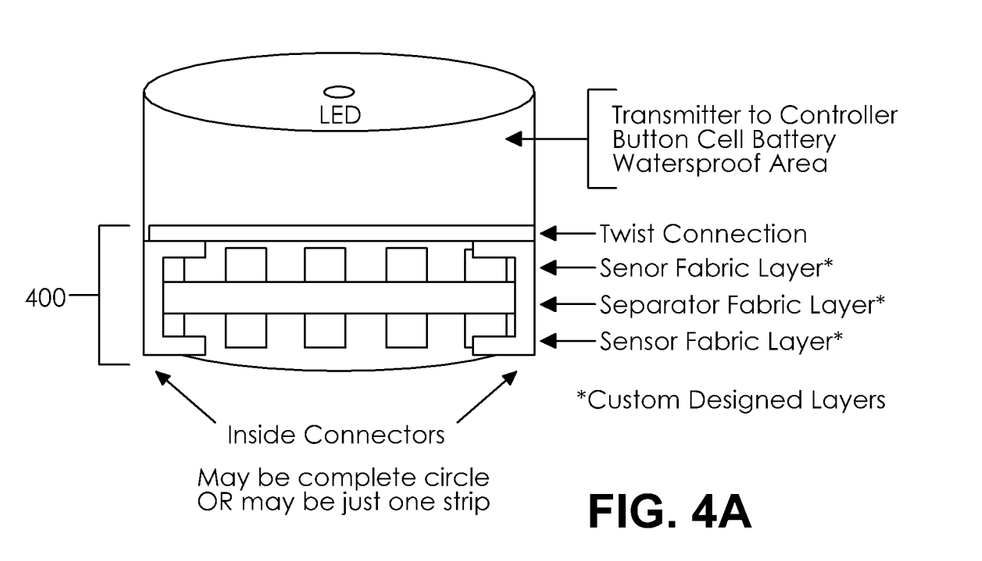
FIG. 4A is an example embodiment of a commercial pad and sensor module of a moisture detection device.
Figure 4B:
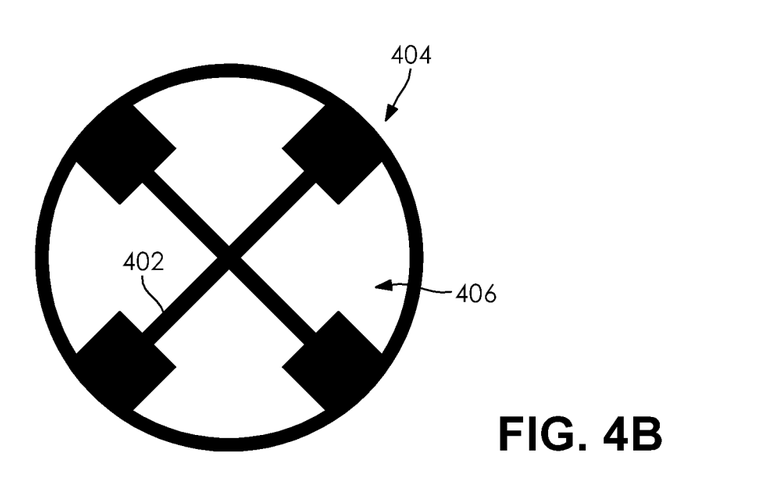
FIG. 4B is bottom view of the sensor of FIG. 4A, according to at least one embodiment.

FIGS. 4A-4B illustrate a portion of a product, according to at least one embodiment, referenced as a pad and a replaceable sensor module 400 of a moisture detection device. The replaceable sensor module has a frame enclosing sensor layers, which are shown below the waterproof area. It attaches to the waterproof area via a twist circular motion. The bottom of the frame 402 is in an "X" shape, in the illustrated embodiment of FIG. 4B. The points of the X are attachment features such as adhesive strips or magnetic elements in part or all. In at least one example, the size is approximately one half inch in height. In FIG. 4B, a raised foot 404 and a sensor fabric layer 406 are shown. It includes a transmitter top portion that is detachable from a multilayer sensor bottom portion. The multilayer sensor component is replaceable in the event of damage or a permanent change in material properties as a result of moisture absorption. The multilayer bottom portion includes two sensor conductive layers surrounding a separator insulating layer. The bottom of the device includes a central "X" where the ends of the X form feet that raise the device to detect moisture present underneath the device, that is then absorbed into the conductive sensor fabric layer. The device includes electrical connectors disposed on the outside portion of the multilayer sensor portion that electrically couples the multilayer sensor to the transmitter portion.

Figure 5A:
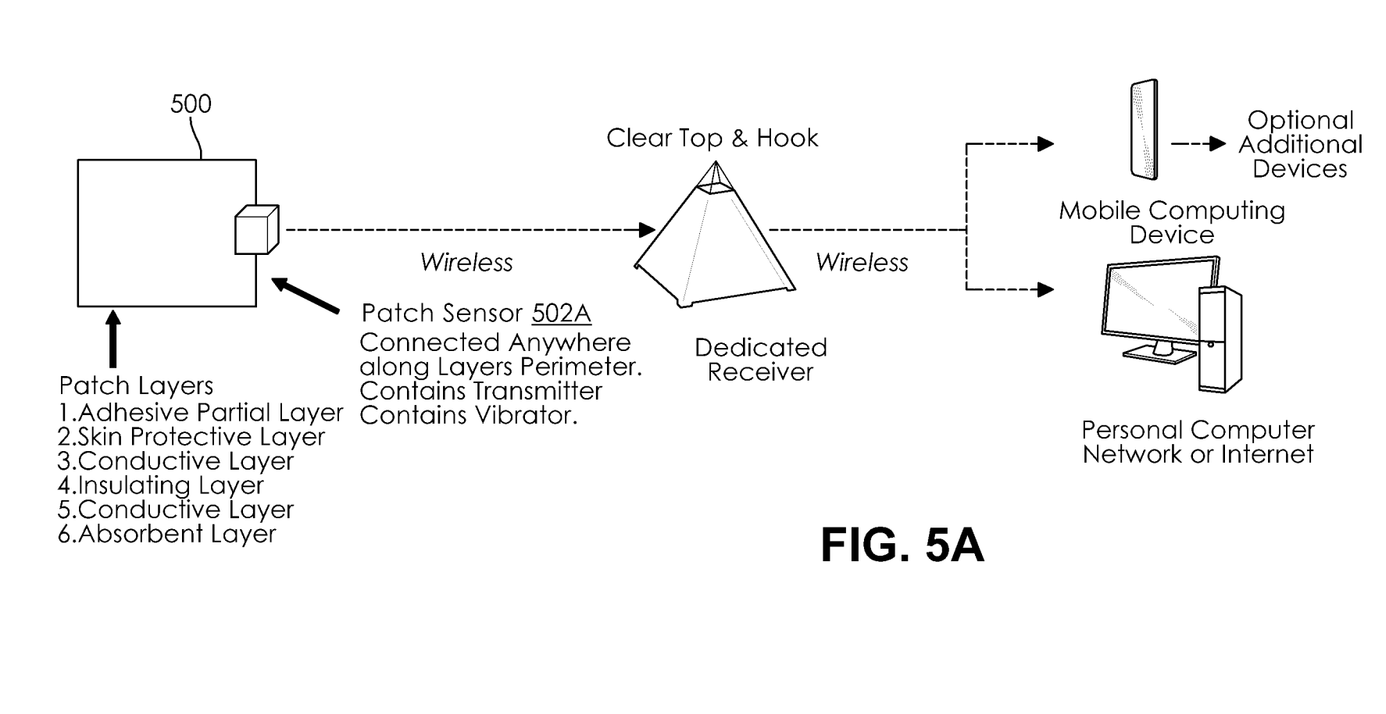
FIG. 5A is an example embodiment of a moisture detection system with a wearable patch containing pad layers, vibrator, transmitter and use of a dedicated receiver.

FIG. 5A illustrates a directly wearable patch 500 with layers and contains a transmitter, a vibrator and is in signal communication with multiple receiving devices. The referenced adhesive partial layer and be used to attached the patch 500 to a host structure and/or the patch sensor 502A (FIG. 5A).

Figure 5B:
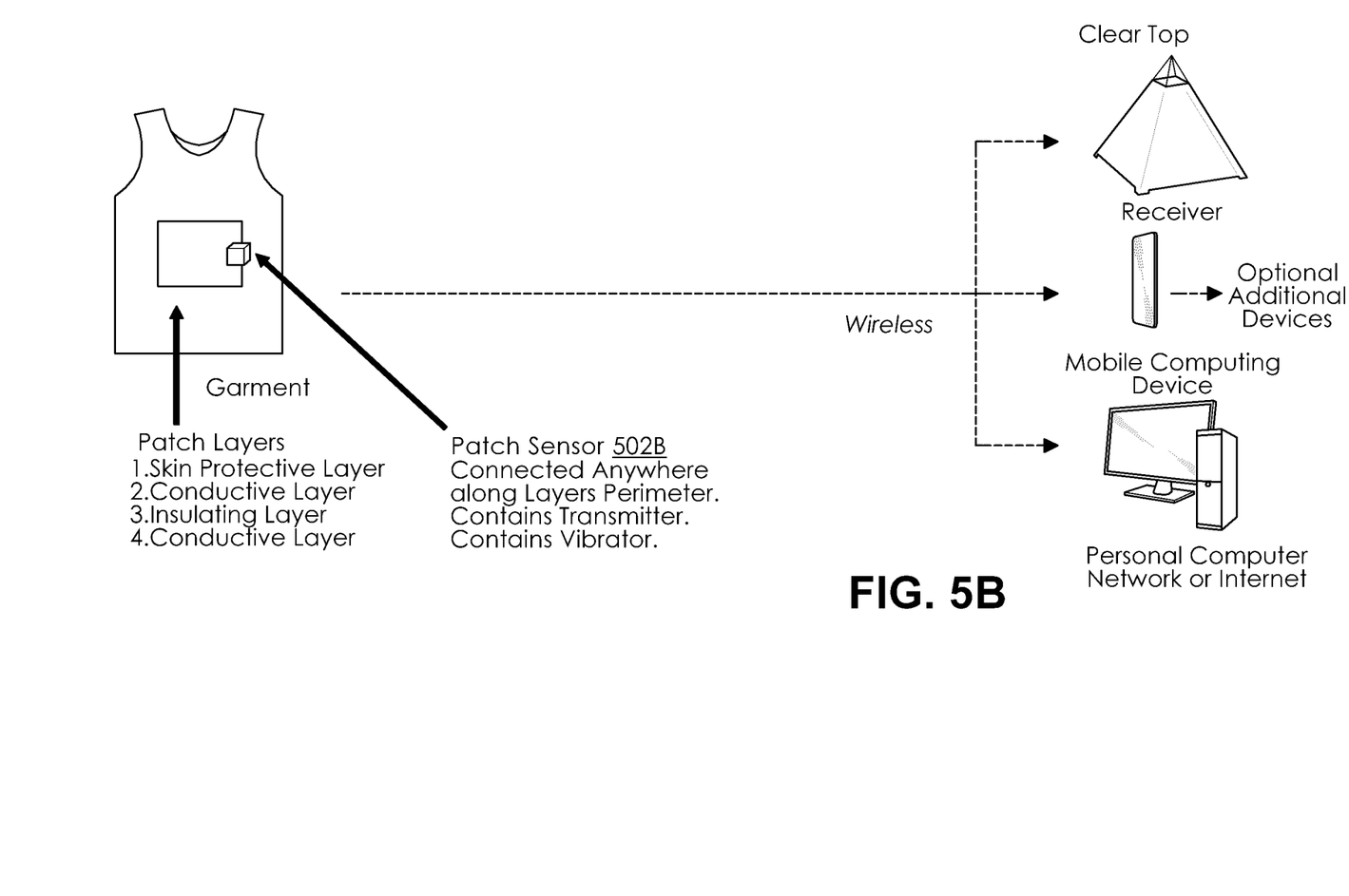
FIG. 5B is an example embodiment of a moisture detection system with a patch on a wearable garment like a shirt/blouse or vest and containing pad layers, vibrator, transmitter and direct connection to mobile and network computers.

FIG. 5B illustrates a patch 510 with layers on a garment 512 like a shirt/blouse or vest and contains a transmitter, a vibrator and is in signal communication with multiple receiving devices.

Figure 6A:
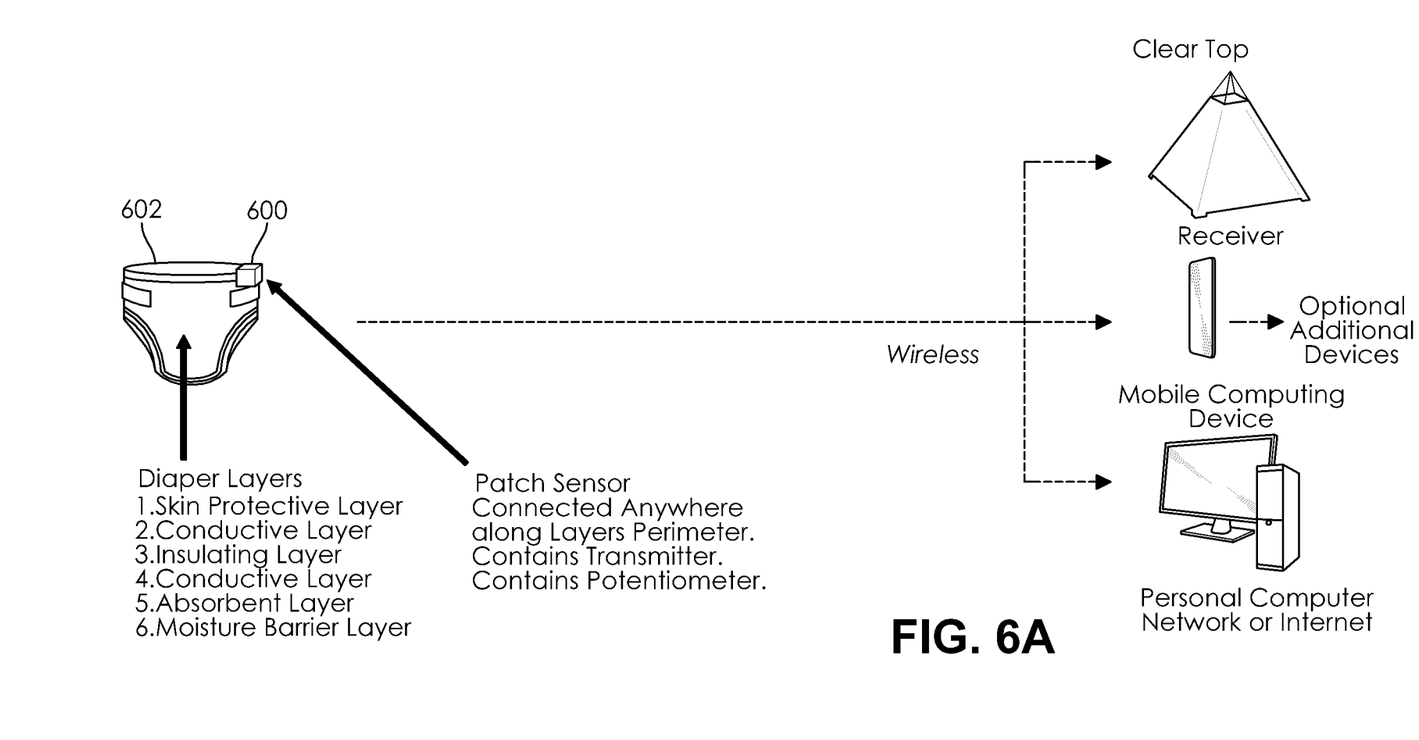
FIG. 6A illustrates a moisture detection system for diapers with additional pad layers and direct connection to mobile and network computers.
Figure 6B:
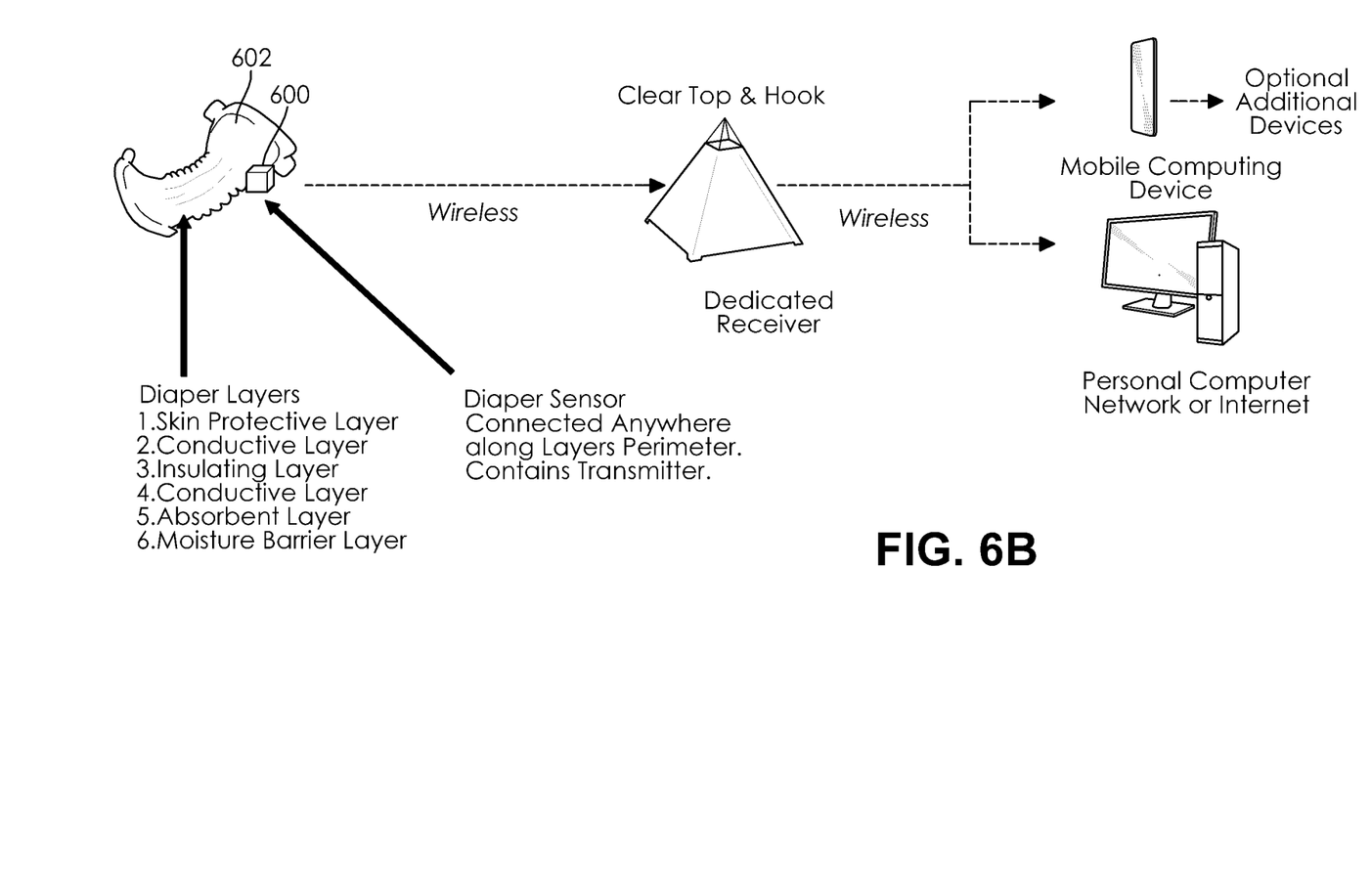
FIG. 6B illustrates a moisture detection system for diapers with additional pad layers and use of a dedicated receiver and connection to mobile and network computers.

FIGS. 6A and 6B illustrate example moisture detection systems for diapers that include: (i) diaper layers that make up a multilayer sensor; (ii) a diaper sensor and transmitter that is electrically coupled to the multilayer sensor; and (iii) one or more receiver devices in signal communication with the transmitter. The multilayer sensor 600 integrated with the diaper 602 can include: (i) a skin protective layer; (ii) a conductive layer; (iii) an insulating layer; (iv) an absorbent layer; and (v) a moisture barrier layer. Those of ordinary skill in the art will appreciate that the configurations shown in FIGS. 6A and 6B are not intended to be limiting, and other system configurations are possible.

Figure 7:
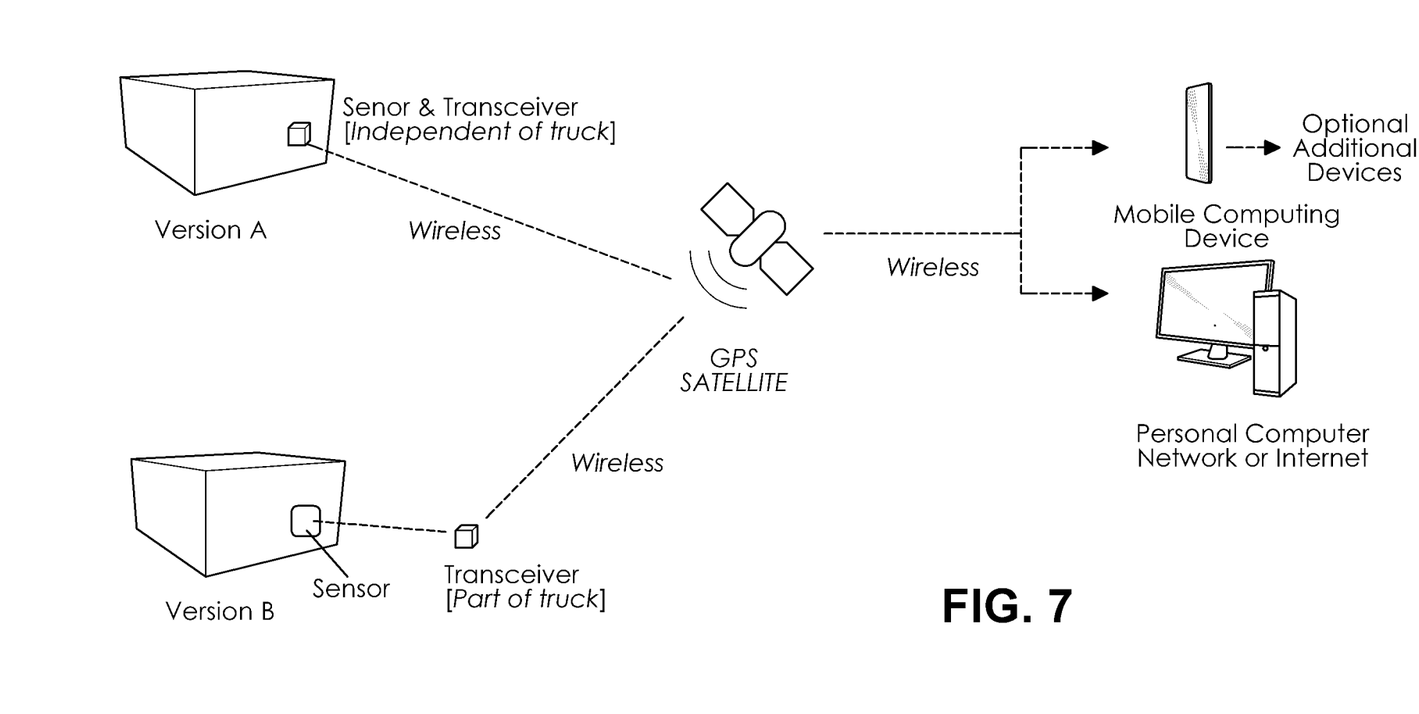
FIG. 7 illustrates an example embodiment of a moisture detection system and a theft detection system for packages employing a transceiver which uses a GPS system to connect to mobile and network computers, according to at least one embodiment.

FIG. 7 illustrates a moisture detection system for packages. A multilayer sensor is affixed as a patch to the inside or outside of the package, or the sensor layers can be incorporated into the packaging top panel, bottom panel, or sidewalls. In context of package delivery, the sensor can wirelessly communicate with a standalone transceiver, a transceiver formed as an integrated unit with the sensor, or a transceiver that is integrated with the delivery vehicle. The sensor detects moisture, and may be a small unit which is attached to the packaging, or can be incorporated into the entire outside layer(s) of the packaging.

When moisture is detected, the transceiver sends a wired or wireless signal to a computing device that generates an alert. The transceiver can also be configured to communicate with a Global Positioning System ("GPS") thereby providing an indicator of the package location as well as the state of moisture detection. That is, the wireless communication between the sensor and the transceiver can utilize short range wireless communication protocols such as Bluetooth® or Near Field Communication ("NFC") such that the geolocation of the transceiver will also reflect the geolocation of the sensor and package. In that instance, the system could also provide a measure of theft detection that allows a package location to be tracked.

Sensor—The sensor can provide an activation signal by wireless short-range to the receiver/controller and to remote networks and receivers. In non-limiting examples, the sensor includes a transmitter and/or vibrator and can be connection anywhere along the perimeter patch or pad.

Sensor Layers—Depending on the particular application, the sensor can be constructed with various types of layers that include, without limitation: (i) a skin protectant layer to provide comfort, cushion, or wicking; (ii) a first conducive layer; (iii) an electrical insulating or separator layer; (iv) a second conducive layer; (v) an absorbent layer; and (vi) a waterproof layer as a moisture barrier. Preferably, the sensor includes at least a first conductive layer, a separator layer and another conductive layer.

Each layer can be homogeneous where the entire layer is conductive, insulating, moisture proof, absorbent, or otherwise demonstrates consistent properties across the entire layer. Alternatively, the layers can be heterogeneous, such as an insulating layer with conductive patches or strips disposed on one surface of the layer.

For applications that touch skin, there are six layers: (i) skin protectant layer; (ii) conductive layer; (iii) insulating layer; (iv) conductive layer; (v) absorbent layer; (vi) moisture barrier layer. The skin protective layer can be formed from cotton, or more preferably, a wicking material that wicks away liquid faster than cotton and dries faster. Wicking refers to a fabric's ability to transport moisture. Examples of suitable wicking materials include performance synthetic fibers such as nylon, acrylic and polyester. Wicking material can be fabric blends that include performance synthetic fabrics in combination with other fabrics, including softer fabrics like cotton. Having a quick drying material prevents stagnate moisture from pooling and causing sores, odors or the buildup of bacteria.

Conductive layers are formed by combining conductive fibers with pulp fibers to form nonwoven webs over the entire layer. The nonwoven conductive layers can be formed using a wetlaid or carded manufacturing process. The wetlaid process is akin to a modified papermaking process where fibers are suspended in water, and various heating, filtering, and vacuum processes are used to separate the water leaving a uniform sheet of material. Wetlaid manufactured materials have the advantage of producing thin, uniform layers.

A carded manufacturing process includes the steps of opening and blending fibers from a source material before transferring the fibers to a card by air transport. The fibers are combed into a web by a carding machine. The web can be parallel-laid, where most of the fibers are laid in the machine direction, or they can be randomized. Typical parallel-laid carded webs result in good tensile strength, low elongation and low tear strength in the machine direction and the reverse in the cross direction.

Needle-punched nonwoven fabrics are made from various fibrous webs (carded webs) in which staple fibers are bonded together mechanically through fiber entanglement and friction after fine needle barbs repeatedly penetrated through the fibrous web. Needle-punched fabrics have characteristic periodicities in their structural architecture that result from the interaction of fibers with the needle barbs. Fiber segments are reoriented and migrated from the surface of the web towards the interior of the fabric, forming pillars of fiber orientated approximately perpendicular to the plane of puncture.

Example formulations for conductive nonwoven materials tested by the present applicant are shown below in Table 1 that utilized carbon fiber materials. The composition figures are shown as a percentage of weight basis. The term "DFP" is Denier per filament equivalent to the weight in grams of 9,000 meters of an individual filament calculated by taking a yard Denier and dividing it by the number of filaments in the yarn.

The formulations include individual layers C1 to C6 formed using a wetlaid process and formulas C7 and C8 representing layers formed with a carded manufacturing process. The layer V1 is a "veiled" layer disposed on conductive material C5 using a needle tacking process that drives needles through the layered materials in the vertical, or "Z" direction, to thereby hold the materials together within a horizontal plane. The resulting conductive layers are labeled as A1 to A3 where conductive layers A2 and A3 utilized one-half inch thick strips of the V1 material spaced one-half inch apart on C5.

The Rayon fibers were selected because of a demonstrated favorable absorbance. The Huvis® material is a binder fiber material that is melted to flow to the surrounding fibers to hold the sheet of conductive material together. PVOH refers to "polyvinyl alcohol" and was used in fiber form.

TABLE 1

| | Conductive Layer Formulations | | | | | | | |
|---|---|---|---|---|---|---|---|---|
| Sample | Tenax® Carbon | 1.5 DPF Rayon® | 25 DPF Rayon® (%) | PVOH Binder | Huvis® 2 DPF | Target Basis (Weight) | Measured Basis Weight | Resistance |
| C1 | 20 | 50 | 25 | 5 | | 200 | 205 | 50 Ω |
| C2 | 10 | 60 | 25 | 5 | | 200 | 202 | 87 Ω |
| C3 | 5 | 65 | 25 | 5 | | 200 | 202 | 320 Ω |
| C4 | 10 | 45 | 25 | | 20 | 200 | 206 | 45 Ω |

TABLE 1-continued

Conductive Layer Formulations

| Label | 1.5 dpf × 38 mm Rayon | | | | | Target Basis Weight (G5M) | Measured Basis Weight (GSM) |
|---|---|---|---|---|---|---|---|
| C5 | 20 | 35 | 25 | 20 | | 215 | 191 Ω |
| C6 | 5 | 50 | 25 | 20 | | 219 | 3 kΩ |
| V1 | 95 | | 5 | | 25 | 25 | 10 Ω |

| Label | 1.5 dpf × 38 mm Rayon | Carbon Fiber ~51 mm | Resistance | Bonding Type | Target Basis Weight (G5M) | Measured Basis Weight (GSM) |
|---|---|---|---|---|---|---|
| C7 | 100 | — | — | Tacked | 200 | |
| C8 | 80 | 20 | 600 Ω | Tacked | 200 | 172 |

| Label | Layer 1 | Layer 2 | Description | Bonding Type | Target Basis Weight (G5M) | Measured Basis Weight (GSM) | Resistance |
|---|---|---|---|---|---|---|---|
| A1 | C5 | V1 | Full sheet tacked | Tacked 4 × | 225 | 226 | 13 Ω |
| A2 | C5 | V1 | ½ strips of veil ½+12 inch apart | through veil | 225 | 214 | — |
| A3 | C5 | V1 | ½ strips of veil ½+12 inch apart | | 225 | 213 | — |

The example formulations shown above are not intended to be limiting. Those of skill in the art will appreciate that other types of fibers can be combined with conductive fibers, including, without limitation, any natural or synthetic cellulosic fibers. A portion of the fibers can be synthetic fibers such as Rayon, polyolefin fibers, polyester fibers, polyvinyl alcohol fibers, bicomponent sheath-core fibers, multi-component binder fibers, and the like.

Additional types of chemicals that may be added to the nonwoven web include, but are not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general, and the like, may also be incorporated into the finished products.

Absorbent layers are preferably thicker than other layers to increase the volume of moisture stored. The absorbent layer can optionally serve to distribute the moisture across an area to prevent transfer of moisture back to a user's skin. Examples of absorbent fabrics and fibers that can be used include rayon, acetate, lyocell, wood and linen. According to further embodiments, the absorbent layer can include cotton blended with another fabric, such as the absorbent materials listed above. An absorbent layer should hold at least one or more times its weight in moisture, but preferably more than 5, 10, 15, or about 20 times its weight in moisture. According to non-preferred embodiments the absorbent layer can include a non-fabric, absorbent polymer positioned within a fabric. Examples of non-fabric polymers can include sodium polyacrylate.

The waterproof layer comprises a material that is impermeable to urine and liquid to prevent liquid from flowing through it and onto the surrounding surfaces. Any suitable waterproofing material can be used for this layer, such as polyurethane, polyvinyl chloride, and the like. The insulating layers can include polyvinylidene fluoride, polypropylene, or polytetrafluoroethylene ("PTFE"), polyester, polyethylene, or polypropylene.

Transmitters—A transmitter, with reference at least to that of pad sensor 104 (FIGS. 1A-1B), transmitter 200 (FIG. 2B), that of patch sensor 502A (FIG. 5A), that of patch sensor 502B (FIG. 5B), that of sensor 600 (FIG. 6A-6B), and that referenced in FIG. 7 as a transceiver, can be electrically coupled to the multilayer sensor through a removable connector, such as male-female plug connector, a pin-connector, a clip connector, a threaded connector, or another suitable electrical connector. The removable connector permits the sensor to be decoupled from the transmitter for cleaning, repair, or replacement of one or both the sensor or transmitter device. The transmitter can also be integrated with the sensor as a single unit or more permanently coupled to the multilayer sensor through a soldered connection or other type of connection. The transmitter can be directly coupled to the sensor or connected to the sensor through a length of insulated wire or cabling to ensure the transmitter is not exposed to moisture or electrical interference near the sensor.

The transmitter can likewise be physically coupled to one or more receiver devices through a permanent or removable connector or through a length of wire or cabling. In other embodiments, the transmitter includes an integrated communication system that is capable of wireless communication with one or more receiver devices. Suitable wireless communication systems can implement communication through radio frequency ("RF"), WI-FI (e.g., wireless local area network products based on the Institute of Electrical and Electronics Engineers 802.11 standards), near field communications ("NFC"), BLUETOOTH®, BLUETOOTH Low Energy ("BLE"), or Ultra-Wide Band ("UWB") and RFID.

The transmitter can simultaneously broadcast signals to one or more receiver devices or be configured to function as a router sending targeted communications to selected receiver devices. The transmitter can include a processor, transitory memory, and non-transitory electronic storage with one or more integrated software applications that implement the described communication functions. With reference to the example system configuration shown in FIG. 2B, a single transmitter 200 can be coupled to multiple sensors and configured by a system user to direct signals from selected sensors to selected receiver devices. In a hospital setting, for example, medical personnel responsible for a set of hospital beds can receive sensor signals from detection devices in those rooms without receiving sensor signals from locations that the personnel are not responsible for monitoring.

The transmitter can receive power through a standard household electrical supply or be powered by a replaceable battery, such as a common three volt (3V) button-cell battery or household AA battery, as non-limiting examples, other battery configurations and sizes can be used. The transmitter can be configured so that the power source is active only when moisture is detected, and the transmitter can include an "on-off" switch to conserve power when the moisture detector device is not in active use. Depending on the technology, a separate power source may not be needed.

The transmitter optionally includes light-emitting-diode ("LED") or other indicators that change color or turn on and off to indicate certain conditions. For example, a LED light might (i) turn green when the transmitter is turned on and functioning normally, (ii) turn red or blink with a particular pattern when the battery needs replacement, or (iii) turn red or blink when moisture is detected. The transmitter can also include other alert or signaling mechanisms, such as emitting an audible, visible, vibratory, or tactile alert that is triggered when moisture or a low-battery condition is detected. An example would be the use of a piezoelectric device that generates vibration and auditory signals at a level in the range of seventy (70) to ninety five (95) decibels. The vibrator may be included as part of or connected to the transmitter and activated when the sensor is activated. The built-in signal devices allow the transmitter to be used in a stand-alone configuration that indicates moisture detection even when the transmitter is not connected to a receiving device.

Receivers—The receiver device can be a dedicated, special purpose device, such as the pyramid device show in FIG. 1A. The dedicated receiver device 102 serves the primary or sole function of system controller and of alerting the detection of moisture through the emission of audible, visible, or tactile alerts. The dedicated receiver device 102 shown in FIG. 1A includes a clear or translucent cover near the top of the device that includes a LED and possibly a piezo within used for signaling. The dedicated receiver device 102 optionally includes a variety of other features, such as an aperture to receive a hook for hanging or mounting or a magnetic base or adhesive strips used for surface mounting such as shown in FIG. 4B.

The receiver device can also be a consumer computing device, such as a cellular smartphone, tablet computer, laptop computer, or desktop computer. The consumer device can include an integrated software application, such as a program, function, routine, applet, or module that permits communication with the transmitter, the sensor, or other receiver devices, and that implements various graphical user interface displays ("GUIs"). The consumer device can be configured to receive system alerts indicating moisture detection, a low battery condition or system updates. Alerts can be received through email, short message service ("SMS") or multimedia messaging service ("MMS") text message, an Internet browser, a "pop-up" alert, or through a dedicated software application (i.e., a "mobile app"), among other means. The integrated software application can also allow consumers to implement other functions, such as directing alerts to certain devices, turning the sensors and transmitters on or off, and recording and reviewing alerts received over time.

The receiver device can also be a network-type device, such as a server used in a commercial application. The receiver devices can also utilize software applications that function using resource available through a third-party provider, such as a Software as a Service ("SasS"), Platform as a Service ("PaaS"), or Infrastructure as a Service ("IaaS") provider running on a third-party cloud service computing device.

Potentiometers—The sensor, with reference at least to sensor 602 in FIG. 6A, can be used in conjunction with a potentiometer that has a variable resistance that can be set to detect various types of fluids and environmental conditions like humidity and temperature. The potentiometer resistance can be calibrated to trigger the complete circuit or the short circuit depending on the fluid absorbed by the insulating layer such as varying the resistance to detect water, urine, perspiration, blood, human stool, coolant or other chemical contaminants and environmental conditions like humidity and temperature. The potentiometer is used to determine when excessive sweating may begin to undermine readiness. It allows adjustment to reflect operating conditions. It may be located anywhere within the system.

In some embodiments, the system functions as a resistor type sensor that monitors the resistance of the circuit formed with the conductive sheet layers and the insulating layer. The system can include a resistance sensing unit that measures a resistance variation between the conductive layer sheets. The resistance sensing unit can be calibrated to detect minute variations in resistance that are known to correspond to different types of materials or fluids, such as calibrating to detect water, urine, blood, perspiration, human stool, coolant or other chemical contaminants as well as various environmental conditions like humidity and temperature. The resistance sensing can have an output signal that varies depending on the detected resistance variation, which allows users to be alerted to the detection of various fluids and other materials.

The sensor can further be configured to operate as a capacitor-type sensor that monitors and detects variations in the capacitance between the conductive layer sheets. A capacitance sensing unit measures a capacitance variation between the conductive layers when moisture is detected on both sensor layers. The material or type of fluid detected is determined according to the type of measured capacitance values obtained by the capacitance sensing unit. That is, the capacitance sensing unit can be calibrated to detect minute variations in resistance that are known to correspond to different types of materials or fluids. The capacitance sensing unit can have an output signal that varies depending on the detected capacitance variation, which allows users to be alerted to the detection of various fluids and other materials and conditions.

Commercial Applications—The moisture detection systems and methods disclosed herein have a wide variety of potential applications where moisture is to be detected and transmitted, such as under pads (e.g., pet pads, pads underneath a person in a bed, pads underneath a person in a wheelchair, etc.), household leak detection (e.g., underneath or adjacent to a sink, air conditioner, hot water heater, sump pump, etc.), children's diapers, adult diapers and incontinence products, commercial or industrial leak detection around equipment (e.g., detect coolant heating or pipe leaks, etc.), or moisture detection on a garment (e.g., detecting perspiration) through use of a patch that is integrated as part of, or attached to, a garment.

For those applications used near human skin or surfaces to be protected from moisture (e.g., use as a diaper, incontinence product, or on a bed or wheelchair), the multilayer sensor portion can include a skin protectant layer and absorbent layer and/or a moisture barrier layer, as discussed above.

Applications such as those shown in FIGS. 5A & 5B include detection of moisture from a person who is perspiring excessively. Excessive perspiration may be caused by one or a combination of factors that include strenuous physical activity, heat, or a medical condition called hyperhidrosis. Hyperhidrosis is abnormally excessive perspiration or sweating that is not necessarily related to heat or exercise. Heavy sweating can cause social anxiety and embarrassment or indication of a medical condition. Excess sweating may be due to other medical conditions, like a heart attack, infections and other medical conditions. The patch is attached to a transmitter, such that when moisture is detected, the transmitter sends a signal received by the receiver, which can then be transmitted to mobile applications or an integrated software application with a personal computer.

Connecting a circuit on a single layer as a hyperhidrosis alert sensor has apparently not been optimal. An underlying problem is that wrinkling or folding the garment produces a false alarm. Use of multiple layers as described herein prevents wrinkled or folded garments from generating false alarms.

Below are examples of nonwoven fabric products to which these descriptions apply. These products can be commercially electrified according to these descriptions and drawings. Electrification of a specially-designed fabric, optionally nonwoven fabric, could act as a trigger for an alarm notification of a potential problem.

Select non-limiting examples are listed below of nonwoven product applications to which electrification can be applied in various embodiments according to these descriptions and the drawings.

Medical—gowns, packaging, suits, wipes.

Filters—allergan membranes, bag filters, laminates, pharmaceutical industry.

Geotextiles—sand bags, erosion control, frost protection, liners.

Other—clothing, composites, tablecovers, cushions, diaperstock, feminine hygiene products, insulation, packaging, tarps.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A moisture detection system comprising:
    a transmitter; and
    a layered sensor connected to the transmitter, the layered sensor comprising a first conductive layer, a second conductive layer, and a separator layer, wherein
        (a) the first conductive layer, the second conductive layer, and the separator layer are approximately planar sheets of material,
        (b) the separator layer is (i) disposed above the first conductive layer and frictionally contacts the first conduct layer, and (ii) disposed below the second conductive layer and frictionally engages the second conductive layer,
        (c) the conductive layers form a closed circuit in a dry state,
        (d) the conductive layers form an open circuit when moisture is present in the separator layer between the first conductive layer and the second conductive layer, and the moisture contacts both the first conductive layer and the second conductive layer, and
        (e) the transmitter detects an absence of a signal from the formerly closed circuit and generates a detection signal.

2. The moisture detection system of claim 1, wherein at least one of the first conductive layer or the second conductive layers comprises at least one of conductive weaves, conductive threads, and carbon fibers.

3. The moisture detection system of claim 1, wherein at least one of the first conductive layer or the second conduct layer comprises wetlaid material formed by combining conductive fibers with pulp fibers to form nonwoven webs.

4. The moisture detection system of claim 1, wherein the system further comprises
    (a) a receiver that receives the detection signal generated by the transmitter, wherein
        (i) the receiver is located in a housing that comprises a translucent portion,
        (ii) the receiver is electrically connected to a light source that is within the housing and that is proximal to the translucent portion, and
        (iii) when the detection signal is received, the receiver turns the light to an on state that shines through the translucent portion.

5. The moisture detection system of claim 1, wherein at least one of the first conductive layer or the second conductive layer comprises an absorbency aid, wherein the absorbency aid comprises at least one of a cationic surfactant, an anionic surfactant, a non-ionic surfactant, a humectant, a plasticizer, low molecular weight polyethylene glycol, a polyhydroxy compound, glycerin, and propylene glycol.

6. The moisture detection system of claim 1, further comprising an output device connected to the layered sensor, wherein the closed or complete circuit results in an electrical signal causing the output device to output an alert.

7. The moisture detection system of claim 6, wherein the output device comprises at least one of a vibrator, a buzzer, and a computing device that displays a notification on an electronic display.

8. The moisture detection system of claim 1, wherein the layered sensor is disposed on an article of clothing.

9. The moisture detection system of claim 8, wherein the layered sensor comprises a moisture wicking layer.

10. The moisture detection system of claim 1, wherein the layered sensor is:
    affixed to an inside or outside of a package for location tracking; or
    is attached to or incorporated in a diaper.

11. A moisture detection system comprising:
    (a) a transmitter;
    (b) a layered sensor electrically connected to the transmitter, the layered sensor comprising a first conductive layer, a second conductive layer, and a separator layer, wherein
        (i) the first conductive layer, the second conductive layer, and the separator layer are approximately planar sheets of material, the separator layer is (A) disposed above the first conductive layer and frictionally engages the first conductor layer, and (B) below the second conductive layer and frictionally engages the second conductive layer, (iii) the two conductive layers form an open circuit in a dry state, (iv) the two conductive layers form a closed or complete circuit when moisture is present in the separator layer between the conductive layers, and the moisture contacts the first conductive layer and the second conductive layer, and (v) wherein the closed or complete circuit results in an electrical signal that is detected by the transmitter, and wherein the transmitter generates a detection signal in response to detecting the electrical signal resulting from the closed or completed circuit.

12. The moisture detection system of claim 11, wherein at least one of the first conductive layer or the second conductive layer comprises at least one of conductive weaves, conductive threads, and carbon fibers.

13. The moisture detection system of claim 11, wherein at least one of the first conductive layer or the second conductive layer comprises wetlaid material formed by combining conductive fibers with pulp fibers to form nonwoven webs.

14. The moisture detection system of claim 11, wherein at least one of the sensor and the transmitter are attached along a perimeter of the layers.

15. The moisture detection system of claim 11, wherein at least the first conductive layer or the second conductive layer comprises and absorbency aid, wherein the absorbency aid comprising at least one of a cationic surfactant, an anionic surfactant, a non-ionic surfactant, a humectant, a plasticizer, low molecular weight polyethylene glycol, a polyhydroxy compound, glycerin, and propylene glycol.

16. The moisture detection system of claim 11, further comprising an output device connected to the layered sensor, wherein the closed or complete circuit results in an electrical signal causing the output device to output an alert.

17. The moisture detection system of claim 16, wherein the output device comprises at least one of a vibrator, a buzzer, and a computing device that displays a notification on an electronic display.

18. The moisture detection system of claim 11, wherein the layered sensor is disposed on an article of clothing.

19. The moisture detection system of claim 18, wherein the layered sensor comprises a moisture wicking layer.

20. The moisture detection system of claim 11, wherein the layered sensor is:
affixed to an inside or outside of a package for location tracking; or
is attached to or incorporated in a diaper.

21. The moisture detection system of claim 11 further comprising a receiver in signal communication with the transmitter, wherein
(i) the receiver receives the detection signal transmitted by the transmitter and outputs the detection signal to a computing device,
(ii) the computing device interprets the detection signal as a positive indicator of moisture,
(iii) the computing device generates a notice displayed on graphical user interface displayed on a display device, and
(iv) wherein the notice is an indicator that moisture was detected.

* * * * *